United States Patent
Anyanwu-Ofili et al.

(10) Patent No.: US 12,051,491 B2
(45) Date of Patent: Jul. 30, 2024

(54) USE OF ARTIFICIAL INTELLIGENCE TO IDENTIFY NOVEL TARGETS AND METHODOLOGIES FOR SKIN CARE TREATMENT

(71) Applicant: Johnson & Johnson Consumer Inc., Skillman, NJ (US)

(72) Inventors: Anuli Anyanwu-Ofili, King of Prussia, PA (US); Khalid Mahmood, Lawrenceville, NJ (US); Nikoleta Batchvarova, West Windsor, NJ (US); Robert Boland, Skillman, NJ (US); Anna Gosiewska, Skillman, NJ (US); Antonius P. J. van den Heuvel, Springhouse, PA (US); Gabriela Oana Cula, Plainsboro, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 601 days.

(21) Appl. No.: 16/794,480

(22) Filed: Feb. 19, 2020

(65) Prior Publication Data

US 2020/0265937 A1 Aug. 20, 2020

Related U.S. Application Data (60) Provisional application No. 62/807,460, filed on Feb. 19, 2019.

(51) Int. Cl.
| | | |
|---|---|---|
| *G16H 20/10* | (2018.01) | |
| *A61K 9/00* | (2006.01) | |
| *G06N 5/04* | (2023.01) | |
| *G06N 20/00* | (2019.01) | |
| *G16H 10/60* | (2018.01) | |

(52) U.S. Cl.
CPC ........... *G16H 20/10* (2018.01); *A61K 9/0014* (2013.01); *G06N 5/04* (2013.01); *G06N 20/00* (2019.01); *G16H 10/60* (2018.01)

(58) Field of Classification Search
CPC ........ A61K 9/0014; G06N 20/00; G06N 5/04; G16H 50/20; G16H 10/60; G16H 20/10
See application file for complete search history.

(56) References Cited

U.S. PATENT DOCUMENTS

| | | | |
|---|---|---|---|
| 6,571,003 B1 | 5/2003 | Hillebrand et al. | |
| 6,761,697 B2 | 7/2004 | Rubinstenn et al. | |
| 6,959,119 B2 | 10/2005 | Hawkins et al. | |
| 7,324,668 B2 | 1/2008 | Rubinstenn et al. | |
| 7,437,344 B2 * | 10/2008 | Peyrelevade | ........ H04N 23/661 |
| | | | 705/26.7 |
| 7,809,601 B2 * | 10/2010 | Shaya | ................ G06Q 30/0641 |
| | | | 705/26.7 |
| 7,950,925 B2 | 5/2011 | McDaniel et al. | |
| 2002/0054714 A1 * | 5/2002 | Hawkins | .............. A45D 44/005 |
| | | | 382/276 |

(Continued)

OTHER PUBLICATIONS

James, William, J., Acne; Clinical practice, N Engl J Med, (2005) 352:1463-1472.;.

(Continued)

*Primary Examiner* — Abdullahi E Salad
(74) *Attorney, Agent, or Firm* — Samuel J. Gee (57) ABSTRACT

Use of an artificial intelligence engine to provide skin care treatment is disclosed.

9 Claims, 6 Drawing Sheets

(56) References Cited

U.S. PATENT DOCUMENTS

| | | | |
|---|---|---|---|
| 2003/0065552 A1* | 4/2003 | Rubinstenn | A61B 5/446 |
| | | | 705/26.7 |
| 2003/0065636 A1* | 4/2003 | Peyrelevade | G06T 11/00 |
| | | | 706/62 |
| 2006/0149570 A1* | 7/2006 | McDaniel | G06Q 30/0601 |
| | | | 705/26.1 |
| 2009/0119234 A1* | 5/2009 | Pinckney | G06N 20/00 |
| | | | 706/12 |
| 2009/0245603 A1* | 10/2009 | Koruga | G06T 7/90 |
| | | | 382/128 |
| 2010/0185064 A1* | 7/2010 | Bandic | A61B 5/444 |
| | | | 600/306 |
| 2012/0288168 A1* | 11/2012 | Srinivasa | G06V 40/16 |
| | | | 382/118 |
| 2015/0339757 A1 | 11/2015 | Aarabi | |
| 2018/0350071 A1 | 12/2018 | Purwar et al. | |
| 2019/0213227 A1* | 7/2019 | Ludwinski | A61B 5/0077 |
| 2019/0237194 A1* | 8/2019 | Salvi | G16H 30/40 |
| 2019/0292577 A1* | 9/2019 | Amini | A61K 31/327 |

OTHER PUBLICATIONS

Kenney, J., et al., Pigmentary disorders in black skin; Clinics in Dermatology (Jun. 1989) 7:2 pp. 1-10; https://doi.org/10.1016/0738-081X(89)90052-7.

Grimes, P. et al., Pigmentary Disorders in Blacks; Dermatologic Clinics (Apr. 1988) 6:271- 81; https://doi.org/10.1016/S0733-8635(18)30673-9.

Kligman, A., et al., A New Formula for Depigmenting Human Skin; Arch. Dermatol., (1975) 111:40-48; 10.1001/archderm.1975.01630130042004.

Hoshaw, R., et al., Ochronosislike Pigmentation From Hydroquinone Bleaching Creams in American Blacks; Arch. Dermatol. (1985) 121:105-8.

Kilkenny M, et al., Acne in Victorian adolescents: Associations with age, gender, puberty and psychiatric symptoms; J Paediatr Child Health (1997) 33:430-433; doi.org/10.1111/j.1440-1754.1997.tb01635.x.

Smithard A, et al., Acne prevalence, knowledge about acne and psychological morbidity in mid-adolescence: a community-based study; Br J Dermatol. (2001) 145:274-279; doi:10.1046/j.1365-2133.2001.04346.x.

Fried, R G, et al., Depression and Skin Disease; Dermatol Clin. (2005) 23:657-664; doi.org/10.1016/j.det.2005.05.014.

Purvis D, et al., Acne, anxiety, depression and suicide in teenagers: A cross-sectional survey of New Zealand secondary school students; J Paediat Child Health, (2006) 42:793-796;.

Vlietstra et al., Using predicate and provenance information from a knowledge graph for drug efficacy screening, J Biomed Semantics. 2018; 9: 23 (2018) pp. 1-10.

International Search Report, PCT/IB2020/051391 Dated: Jul. 3, 2020.

* cited by examiner

USE OF ARTIFICIAL INTELLIGENCE TO IDENTIFY NOVEL TARGETS AND METHODOLOGIES FOR SKIN CARE TREATMENT

BACKGROUND OF THE INVENTION

FIELD OF THE INVENTION

Human Skin

The skin is the body's largest organ. It covers and protects the body. Skin maintains water and electrolyte balance; is a physical barrier that protects underlying tissues from injury, UV light, and bacterial invasion; helps with feeling, e.g., heat, cold, pain, pressure and touch; perceives and informs the brain of changes in the environment; maintains body temperature; and assists with making vitamin D.

Medications used to treat skin conditions include topical and oral drugs. Some common topical treatments for skin conditions include: antibacterials, including mupirocin or clindamycin, which are often used to treat or prevent infection; anthralin, which helps reduce inflammation and can help treat psoriasis; antifungal agents, including clotrimazole (Lotrimin), ketoconazole (Nizoral), and terbinafine (Lamisil AT), which are topical antifungals; benzoyl peroxide and creams, gels, washes and foams containing benzoyl, which are used to treat ringworm and athlete's foot; peroxide, which is used to treat acne; coal tar, which is used to treat conditions including seborrheic dermatitis (usually in shampoos) or psoriasis; corticosteroids, which are used to treat skin conditions including eczema; crisaborole (Eucrisa), which is used to treat mild to moderate eczema; retinoids, including Retin-A and Tazorac, which are used to treat conditions including acne; salicylic acid, which is the active ingredient in many skin care products for the treatment of acne and warts. Some common oral or injection treatments for skin conditions include: oral antibiotics, including dicloxacillin, erythromycin and tetracycline; antifungal drugs, including fluconazole and itraconazole, which are used to treat more severe fungal infections; antiviral agents, including acyclovir (Zovirax), famciclovir (Famvir) and valacyclovir (Valtrex), which are used for skin conditions including those related to herpes and shingles; corticosteroids, including prednisone, which are used to treat skin conditions linked to autoimmune diseases including vasculitis and inflammatory diseases such as eczema; immunosuppressants, including azathioprine (Imuran) and methotrexate (Trexall), which are used to treat conditions including severe cases of psoriasis and eczema; biologics, including adalimumab (Humira), adalimumab-atto (Amjevita), a biosimilar to Humira, brodalumab, (Siliq), etanercept (Enbrel), etanerceptszzs, (Erelzi), a biosimilar to Enbrel, infliximab (Remicade), ixekizumab, (Taltz), secukinumab (Cosentyx) and ustekinumab (Stelara), which are the latest methods being utilized to treat psoriasis and other conditions; enzyme inhibitors, including apremilast (Otezla), which is used to treat inflammation, and Eucrisa, which is used to treat mild to moderate atopic dermatitis/eczema; retinoids, including Acetretin (Soriatane), which is specifically used to treat all types of severe psoriasis.

Accordingly, a need exists for new approaches in diagnosing and treating skin conditions.

Acne

Unwanted dermatological disorders often associated with the production or over production of sebum are well known. One such dermatological disorder includes acne vulgaris (acne), which is the most common dermatological disorder treated by physicians. Acne vulgaris is an inflammatory disease of the pilosebaceous glands characterized by an eruption of the skin, often pustular in nature but not suppurative. One common bacteria associated with this disease is *Propionibacterium acnes*. Acne is a common affliction of the adolescent and affects a small but significant percentage of the adult population. Acne lesions are of four basic types: comedones (blackheads or whiteheads), papules, pustules, and cysts (or nodules). Acne inflammatory disease results in unsightly lesions, particularly on the face, and in some cases results in severe scarring. Microbes, including or related to acne, exist that cause harm or disease in living tissues of humans and animals.

It is estimated that as many as 32 million Americans exhibit some form of unwanted acne. Acne affects more than eighty-five percent of teenagers, and although acne most commonly occurs during adolescence, the condition may continue into adulthood. (William, J., N Engl J Med, (2005) 352:1463-1472.)

Acne is an inflammatory dermatological disorder affecting the pilosebaceous units of affected subjects. Acne is cause by bacteria that infects the hair follicles, which in turn leads to the formation of comedones composed of sebum, keratin and further proliferation of microorganisms, which include for example, *Propionibacterium acnes* (*P. acnes* or *P. acneis*). It is further believed that *P. acnes* plays a role in the digestion of the sebum and keratin present in the comedones into inflammatory by-products which are responsible for further irritating the affected hair follicle, thereby resulting in further inflammation, the formation of abscesses or cysts, which in severe cases may lead to scarring.

In many affected subjects, acne scarring and/or post-inflammatory hyperpigmentation (PIH) occurs as a result of inflammation of the pilo-sebaceous unit (PSU), and in some cases the scarring can be permanent. Subjects affected by PIH generally present with irregular, darkly-pigmented spots occurring after inflammation due to a skin insult such as, for example acne. In some individuals, PIH may resolve slowly but may persist for months. (Kenney, J., et al., Clinics in Dermatology (1989) 7:1-10; Grimes, P. et al., Dermatologic Clinics (1988) 6:271-81). Although the pathogenesis underlying PIH is relatively well-understood, available therapies for PIH remain unsatisfactory and currently available therapies, which include, for example the use of hydroquinones as bleaching agents and/or retinoids, can result in depigmentation, irritant dermatitis, and ochronosis (McDonald, C., Prog. in Dermatol. (1973) 4:15-20; Kligman, A., et al., Arch. Dermatol., (1975) 111:40-48; and Hashaw, R., et al., Arch. Dermatol. (1985) 121:105-8).

The complications of acne are not limited to the skin of affected subjects. The physical symptoms of acne may contribute to the development of emotional and psychological distress, depression, anxiety and increased risks of suicide. (See, e.g., Kilkenny M, et al., J Paediatr Child Health (1997) 33:430-433; Smithard A, et al., Br J Dermatol. (2001) 145:274-279; Fried, R G, et al., Dermatol Clin. (2005) 23:657-664; and Purvis D, et al., J Paediat Child Health, (2006) 42:793-796.) The emotional distress which is caused by, or is otherwise aggravated by, the symptoms of acne may be particularly troublesome for adolescent subjects.

Various topical agents are utilized in the treatment of acne and these include sulfur, resorcinol, salicylic acid, benzoyl peroxide, retinoids and topical antibiotics. For example, commercially available topical treatments include both prescription and over-the-counter treatments, such as benzoyl peroxide to kill bacteria and dry the skin, salicylic acid to help unclog follicles, and sulfur. The topical use of retinoids to facilitate shedding of skin in an effort to help unclog follicles is also used to treat affected individuals.

Systemically available treatments have also been used to treat acne, including, for example tetracycline antibiotics such as minocycline. Generally, subjects are prescribed an extended course of antibiotic therapy and despite such extended therapies, the recurrence rate in these subjects is often high. Prescription antibiotics are also associated with a slow onset of action, which can lead to poor patient compliance.

Oral retinoids, such as isotretinoin, may also be effective; however their use is generally reserved for severe cases of acne due to the association of serious side effects, which may include teratogenicity, depression and suicidal ideation. Many of the available acne treatments are expensive and may cause considerable adverse effects. Furthermore, some medications may require continuous therapy and/or subjects may not promptly respond to such therapy or only achieve limited improvements during treatment.

Accordingly, novel and effective therapies are needed for the treatment of acne, and in particular novel topical therapies that improve symptoms in a safe, rapid and effective manner are needed. There is also a need for treatments that are safe and that can be safely applied for extended periods of time and for treatments that quickly resolve the signs and symptoms of a dermatological disorder.

The invention relates to methods, combinations, apparatuses, systems, and articles of manufacture for identifying novel targets and methodologies for skin care treatment. In one aspect, the invention may employ an artificial intelligence engine to identify novel targets and methodologies for treatment of acne vulgaris.

DESCRIPTION OF RELATED ART

Although the invention, in its broadest sense, is not limited to any particular products, for purposes of explaining some inventive features and principles, the invention is described herein in connection with personal care products.

U.S. Pat. No. 6,761,697 to L'Oreal discloses a method for predicting evolution of at least one condition of an external body portion of a subject.

U.S. Pat. No. 7,324,668 to L'Oreal discloses a method of performing a skin analysis and maintaining a subject's privacy.

U.S. Pat. No. 7,437,344 to L'Oreal S. A. discloses a method of providing beauty advice.

U.S. Pat. No. 7,950,925 to Kimberly Clark discloses a method for educating a consumer about a personal care product that includes receiving a request from a consumer for information regarding a personal care product and receiving from the consumer a description of one or more physical characteristics associated with the consumer and related to the personal care product.

U.S. Pat. No. 6,959,119 to Unilever Home & Personal Care USA discloses a method for identifying progress of a cosmetic product treatment affect upon a consumer.

U.S. Pat. No. 6,571,003 to Proctor & Gamble discloses a method for locating one or more visual skin defects on a portion of a person.

SUMMARY OF THE INVENTION

In accordance with an aspect of the invention, an artificial intelligence engine may be employed to aid in identifying novel targets and methodologies for skin care treatment. In one embodiment, the novel target or methodology identified is used to develop products or recommendations for skin care treatment of acne vulgaris.

DETAILED DESCRIPTION OF THE INVENTION

Definitions

"Artificial intelligence" is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the AI engine may learn to adapt to unknown and/or changing environment for better performance.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process, or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

Forms of the word "displaying" and like terms may also include indirect acts such as providing content for transmission over a network to a display device, regardless of whether the display device is in the custody or control of the sender. Any entity in a chain of delivering information for display performs an act of "displaying", as the term is used herein.

"Enabling", "facilitating", and "causing" an action refer to one or more of a direct act of performing the action, and any indirect act of encouraging or being an accessory to the action. Other examples of indirect activity encompassed within the definitions of "enabling", "facilitating", and "causing" may include providing a subject with one or more of tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling access" and "enabling display" do not necessary require that the actor actually access or display anything. For example, the actor may perform the enabling function by affiliating with an entity who performs the action, or by providing instructions, tools, or encouragement for another to do the accessing and displaying.

The term "image" may include one or more of two-dimensional and three-dimensional representations. In certain examples consistent with the invention, a plurality of images from different perspectives may be used to construct a three-dimensional image. In a broader sense, only a single image may be used. Depending on the embodiment, the term "image" may include either a visually perceptible image or electronic image data that may be either used to construct a visually perceptible image or to derive information about the subject. The image may be a body image corresponding to an anatomical portion of the subject, and may represent, for example, the subject's entire face, or a portion of the subject's face. The image may be a detailed picture (e.g., a digital image or a photograph) of a portion of the subject's body and/or a topological plot mapping contours of a portion of subject's body. If the image is representative of an external body condition, the image could be either an actual image showing the condition or an image including symbolizations of the condition, for example. The image may be an actual or a simulated image. Simulated images may include wholly or partially generated computer images, images based on existing images, and images based on stored features of a subject.

The term "image capture device", similar terms, and terms representing structures with similar functions may include one or more of a digital camera, webcam, film camera, analog camera, digital video camera, scanner, facsimile machine, copy machine, infrared imager, ultra-sound imaging device, or any other mechanism for acquiring an image of a subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

Forms of the word "maintain" are used broadly to include gathering, storing, accessing, providing access to, or making something available for access, either directly or indirectly. For example, those who maintain information include entities who provide a link to a site of a third party where the information is stored.

The term "network interface" or similar terms, refer to any mechanism for aiding communications between various nodes or locations in a network. A network interface may include, for example a bus, a modem, or any other input/output structure. A network interface may permit a connection to any network capable of being connected to an input and/or output module located within at least one or more of the following exemplary networks: an Ethernet network, an Internet Protocol network, a telephone network, a radio network, a cellular network, or any mechanism for permitting communication between two or more modes or remote locations. In some invention embodiments, a network interface might also include a user interface.

"Product" is used broadly to refer to one or more of the following: tangible merchandise (cosmetic, non-cosmetic, device), services (skin care treatment applications), diagnostics, skin care treatment regimen (e.g., a combination of merchandise and/or services), opinions, instructions, and/or relevant information.

The term "providing" includes direct and indirect activities. For example, providing access to a computer program may include at least one of providing access over a network to the computer program, and creating or distributing to the subject a computer program configured to run on the subject's workstation or computer. For example, a first party may direct network traffic to (either through electronic links or through encouragement to visit) a server or web site run by a second party. If the second party maintains a particular piece of software thereon, then it is to be understood that within the meaning of "providing access" as used herein, the first party is said to provide access to the particular software. Or if the first party directs a subject to a second party who in turn ships the particular software to the user, the first party is said to provide the user with access to the particular software. (Of course, in both of the above instances, the second party would also be providing access within the meaning of the phrase as used herein.)

"Receiving" may include at least one of acquisition via a network, via verbal communication, via electronic transmission, via telephone transmission, in hard-copy form, or through any other mechanism enabling reception. In addition, "receiving" may occur either directly or indirectly. For example, receipt may occur through a third party acting on another party's behalf, as an agent of another, or in concert with another. Regardless, all such indirect and direct actions are intended to be covered by the term "receiving" as used herein. A received request, for example, may take one of many forms. It may simply be a checked box, clicked button, submitted form or oral affirmation. Or it might be a typed or handwritten textual request. Receiving may occur through an on-line interest form, e-mail, facsimile, telephone, interactive voice response system, or file transfer protocol transmitted electronically over a network at a web site, an internet protocol address, or a network account. A request may be received from a subject for whom information is sought, or an entity acting on the subject's behalf. "Receiving" may involve receipt directly or indirectly through one or more networks and/or storage mediums. Receipt may occur physically such as in hard copy form, via mail delivery or other courier delivery.

The term "network" may include a public network such as the Internet or a telephone network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding or including voice transmission.

Examples of "service" forms of skin care treatment include massages, facial rubs, deep cleansings, applications of skin care treatment product, exercise, therapy, or any other action effecting the external body condition whether performed by a professional, the subject, or an acquaintance of the subject.

The terms "skin care treatment recommendation", "skin care treatment guidance", and similar terms are used interchangeably to refer to the provision of skin care treatment related information to a subject. Recommendation or guidance includes one or more of skin care treatment product recommendations, remedial measures, preventative measures, predictions, prognoses, application and use information, suggestions for complementary products, lifestyle or dietary recommendations, or any other information intended to aid a subject in a course of future conduct, to aid a subject in understanding past occurrences, to reflect information about some future occurrences related to the subject's skin care treatment or to aid a subject in understanding skin care treatment products, as defined above.

The term "skin condition" is anything that irritates, clogs, or inflames skin and/or causes symptoms such as redness, swelling, burning, and itching. Allergies, irritants, a person's genetic makeup, and certain diseases and immune system problems can cause rashes, hives, and other skin conditions. Many skin problems, such as acne, can also affect a person's appearance.

The term "user interface" may include at least one component such as a keyboard, key pad, mouse, track ball, telephone, scanner, microphone, touch screen, web cam, interactive voice response system (IVR), voice recognition system or any other suitable input mechanism for conveying information. A user interface may also include an input port connected by a wired, optical, or wireless connection for electromagnetic transmissions. In some embodiments, a user interface may include connections to other computer systems to receive the input commands and data therefrom. User interface may further include a data reading device such as a disk drive for receiving input data from and writing data to storage media such as magnetic and optical disks.

Consistent with the concepts set forth above, all other recited actions such as, for example, obtaining, determining, generating, selecting, applying, simulating, presenting, etc., are inclusive of direct and indirect actions. Thus, for purposes of interpreting the following claims, an entity performs a recited action through either direct or indirect activity. Further examples of indirect activity include sending signals, providing software, providing instructions, cooperating with an entity to have the entity perform the action, outsourcing direct or indirect actions, or serving in any way as an accessory to the specified action.

Reference will now be made in detail to the invention, examples of which are illustrated in the accompanying drawings. The same reference numbers may be used throughout the drawings to refer to same or like parts.

Example

The Euretos AI platform was employed to assess molecular mechanisms that influence cell and tissue functions, and in turn mediate phenotypes and disease pathology, in order to identify novel targets and methodologies to treat acne vulgaris. The Euretos AI platform integrates and interconnects the following three types of data sources:

Life sciences databases, i.e., sources that life scientists directly consult some of which are widely known such as Pubmed, Uniprot, Chembl and many other biological sources.

Textual and publication sources, i.e., text based sources such as Pubmed, patent data and clinical records.

Semantic and ontological sources, i.e., sources like ontologies, structured vocabularies and thesauri that play a role in classifying life sciences data and recognizing individual concepts.

(See Euretos Data Sources Overview, http://www.euretos.com/files/EuretosSources2018.pdf).

In order to better understand the molecular mechanisms of acne, a literature search of acne-related public data sets was conducted; pertinent data was analyzed to identify common elements, genes and biological pathways; a disease mechanism based on nuclear receptor balance was proposed, e.g., it is believed that imbalance of this network leads to acne; machine learning was employed to model the effect of key proteins in nuclear receptor balance on acne lesion expression signature; and machine learning was employed to identify target candidates that could be used in the treatment of acne.

Upregulated (1) receptors on the cell and (2) cell originating signal are potential treatment targets. Using expression data in GEO (gene expression omnibus) a simulation model was built based on dependencies in expression patterns. Key nuclear receptors and their co-regulators were highlighted in the disease hypothesis and integrated in machine learning efforts. The disease mechanism hypothesis was used to improve models and predictions.

In order to better understand systemic influences on acne, machine learning was employed to predict acne lesion expression signature by modulating the key protein network. It was hypothesized that compounds that have an expression profile that is highly correlated with acne lesions and their targets that have high modulating effect on nuclear receptors may be modulated by systemic molecules. Differential expression in acne lesions was compared to dermal cell types to confirm that sebocytes and macrophages act as major players in acne. Hypothesized that compounds that are potential treatments for acne have an expression profile that is anti-correlated with the differential expression between lesion and non-lesion in acne patients.

In order to identify new target candidates, machine learning was employed to predict counter-expression signature effects (via concept mapping (CMAP) correlation) and to classify target candidates for efficacy. In order to identify natural product candidates, a systematic search was conducted to identify molecules that (1) are ingredients of "natural" food or cosmetic products; and (2) include mechanisms of action for multi-target treatment strategies.

Systemic influences in acne were analyzed and verified through computer simulation.

In accordance with the invention, a data driven, computational systems biology approach to target and biomarker discovery that takes the cellular and molecular mechanisms underlying disease etiology and progression as its starting point has been implemented. In accordance with the invention, the Euretos AI Platform (EAIP), which combines over 250 integrated sources with various computational approaches, including best in class machine learning with close to 80% accuracy, was employed to identify natural ingredients and targets for acne vulgaris as a therapeutic approach. (See Vlietstra et al., Using predicate and provenance information from a knowledge graph for drug efficacy screening, J Biomed Semantics. 2018; 9: 23 (2018); and Euretos Knowledge Platform White Paper, http://files.massbio.org/file/yo0Cpzl.WEnwBZcK8bh.2.pdf).

Biological investigation and AI track focusing on machine learning were employed to propose a disease mechanism (Phase 1), which was then utilized in machine learning (Phase 2) to improve models and predictions. An integrative meta-analysis of public data sets was performed to investigate acne and related cell types. Common elements, genes, and biological pathways were identified to uncover the disease mechanism. Information in public data sets were enriched with the connections in the Euretos AI platform. The EAIP cell type expression library enabled the deconvolution of gene expression profiles into specific cell types. Differential expression in acne lesions was compared to dermal cell types to confirm that sebocytes and macrophages act as major players in acne.

Results

Out of 516 candidate targets, the EAIP effectively predicted 103 genes. (See Table 1 below). Five out of the ten genes with highest probabilities for effectiveness were nuclear receptors, supporting a disease hypothesis. Although some of the nuclear receptors have established roles in acne, EAIP predicted several other nuclear receptor family members, previously not linked to acne, to be effective targets. EAIP classifier model highlighted some established targets, such as the NF-kappa-B pathway, which is activated by multiple stimuli such as inflammatory cytokines, bacterial products, or other cellular stresses.

TABLE 1

| Gene |
| --- |
| RELA |
| NFKB1 |
| MYC |
| NR2F2 |
| PPARA |
| NR2F1 |
| NR4A1 |
| NR5A1 |
| RUNX1 |
| NFE2L2 |
| KNG1 |
| IKBKB |
| PKM |
| NR1H4 |
| GAPDH |
| TGFBR2 |
| TTR |

TABLE 1-continued

| Gene |
| --- |
| ESRRA |
| MDM2 |
| RHOA |
| NR4A2 |
| KEAP1 |
| BRCA1 |
| CRKL |
| ARNT |
| ALPI |
| NLRP3 |
| ZFP36L1 |
| CDK2 |
| SMAD3 |
| CREBBP |
| NEK5 |
| FPR1 |
| UHRF1 |
| THPO |
| CDK1 |
| MTOR |
| NPSR1 |
| NR1H3 |
| NR1H2 |
| SLC29A3 |
| EGF |
| HLA-DRA |
| PLK1 |
| PER2 |
| SELE |
| TSKU |
| AK4 |
| HIF1A |
| NFKBIB |
| PRKD1 |
| PAK6 |
| ZAK |
| DCLK3 |
| LIMK1 |
| ERCC1 |
| BRAF |
| MAPK14 |
| CDK18 |
| CXCR2 |
| NEK2 |
| TNFRSF1A |
| CDK9 |
| PIK3CA |
| SELP |
| PNRC1 |
| TREM1 |
| PDIA5 |
| MERTK |
| PAFAH1B2 |
| MAP2K2 |
| PAFAH1B3 |
| DAPK3 |
| CHEK1 |
| STK32B |
| IL10RA |
| AURKA |
| TSSK1B |
| PSMD14 |
| DCLK2 |
| NCOA3 |
| FGFR1 |
| CLEC16A |
| IGHMBP2 |
| ACVRL1 |
| NAE1 |
| LCN2 |
| IDH1 |
| CD28 |
| DUSP1 |
| POLI |
| FLJ45079 |
| GDF15 |
| CD163 |
| PTK2 |

TABLE 1-continued

Gene

NUAK2
CDK7
IGF1R
CASP3
APOBEC3F
ACKR1
ABCC1
PIAS2

Nuclear Receptors

The list of predicted effective targets included a large representation of nuclear receptors with high probabilities (over 0.9). In Top10 genes predicted effective, five encoded for members of the nuclear receptor family: NR2F2, PPARA, NR2F1, NR4A1, NR5A1. Except for PPARA, the roles of these nuclear receptors in acne have not been suggested before. NR5A1 encodes for steroidogenic factor 1, but the functions of NR2F2, NR2F1, and NR4A1 have not been characterized. Three out of the five genes mentioned above emerged from the CMAP analysis, confirming that their perturbation leads to an acne-like expression pattern. Connections between four of the genes and RXRs have been found in the Euretos AI platform, indicating that these genes participate in the nuclear receptor network.

A natural ingredients analysis was conducted to identify natural agents affecting many nuclear factors simultaneously. (See attached Excel document.) Starting with the five genes in the Top10 of the effective group, 115 natural compounds in total were identified. Most of the natural ingredients targeted PPARA and NR5A1, reflecting the more extensive studying of these genes compared to the other three. Quercetin, genistein, and vitamin e, which affected the most targets, are of interest in acne treatment.

In addition, other nuclear receptor-related factors appeared as effective targets: ESRRA (Prob 0.81), NR1H4 (Prob 0.84), NR4A2 (Prob 0.81), NR1H3 (Prob 0.73), NR1H2 (Prob 0.73). This family appears to be central to the acne pathology, possibly through the extensive interplay between the family members.

NF-kappa-B

The classifier model indicated that inflammatory genes are effective targets for treating acne: the subunits of NF kappa B had the highest probabilities according to the model. Interestingly, the gene for subunit RelA (RELA) had higher probability and gene-disease score for acne than the gene NFKB1. In support for the central involvement of NF-kappa-B signaling in acne, the inhibitor of nuclear factor kappa B kinase subunit beta, encoded by IKBKB, was predicted to be an effective target as well, with a probability of 0.85. NF-kappa-B signaling pathway is activated by multiple stimuli such as inflammatory cytokines, bacterial products, or other cellular stresses. Inhibiting this inflammatory pathway might be necessary in acne treatment to decrease systemic inflammation. The Euretos AI platform identified several natural ingredients with the potential to inhibit both NFKB1 and RELA: niacin zinc salt, vitamin e, docosahexaenoic acid, and cis-resveratrol. From these compounds, cis-resveratrol inhibits also IKBKB.

NFE2L2 and KEAP1

NFE2L2, a major regulator of antioxidative stress response, was predicted as an effective target with a high probability of 0.88. NFE2L2 encodes for an abundantly expressed transcription factor responding to oxidative stress and environmental agents. NFE2L2 is upstream of HIF1A, which was also classified as an effective target with a modest probability of 0.66. Both of these transcription factors work together in redox balance. NFE2L2 induces expression of genes involved in detoxification, while it remains inactive in the absence of stimuli by the action of its repressor, KEAP1. KEAP1 binds to NFE2L2 preventing its translocation to the nucleus, and targets NFE2L2 to the proteasomal system. Furthermore, also KEAP1 was predicted as an effective target in acne treatment with a probability of 0.81.

NFE2L2 is annotated to metabolic diseases such as diabetes, cardiovascular diseases, and obesity. The induction of cytoprotective genes by NFE2L2 may protect the skin from developing a pathological state, thus stimulation of this gene might be beneficial in acne treatment. Thus natural ingredients activating NFE2L2 and inhibiting KEAP1 may be of interest. In this context, cinnamaldehyde has been presented as a treatment option for acne. In addition, the Euretos AI platform identified several other natural ingredients affecting NFE2L2 and the gene product, such as silymarin, sulforaphane, resveratrol, docosahexaenoate, and berberine. All but berberine simultaneously inhibit KEAP1. As these proteins react to the redox balance, several natural antioxidants can affect their activity.

ALPI

ALPI encodes for intestinal-type alkaline phosphatase, which is expressed specifically in the gut. Despite no publication reporting connection of ALPI to acne, it was predicted as an effective target with a relatively high probability (0.78). The enzymatic activity of this protein dephosphorylates bacterial endotoxin lipopolysaccharide in the gut lumen, thus ALPI is plays a role in gut homeostasis and host-microbiome interactions. Decreased ALPI expression or function is associated with intestinal inflammation, dysbiosis, and subsequently systemic inflammation, possibly due to decreased regulation of mucosal permeability with the loss of ALPI. In addition to its linkage to systemic inflammation, ALPI seems to connect to acne through diet-related effects, especially through effects in glucose metabolism. The typical Western diet, which is also blamed for acne, reduces ALPI activity, while increasing this activity would improve glucose tolerance. The prediction of ALPI as an effective target further supports the role of diet and gut homeostasis in acne etiology.

Possibly due to the association of ALPI with several gut-related diseases, several reports have investigated the effects of food compounds in ALPI activity. Indeed, the expression of ALPI can be increased with several natural ingredients: curcumin, vitamin d and vitamin k2.

Investigation in the Euretos Platform revealed a result from the Binding database reporting that camyna stimulates intestinal-type alkaline phosphatase: camyna is a synonym for tioxolone, which is an anti-acne preparation. Further database mining indicated that natural compounds myricetin and 5,6,7,8,4'-pentahydroxyflavone stimulate the activity of intestinal-type alkaline phosphatase.

Recommendation for Skin Care Treatment

The invention may be used to aid consumers in obtaining skin care treatment recommendation. That is, based on user-specific information, the invention may provide a consumer skin care treatment recommendation, such as recommended products.

Figure 1:
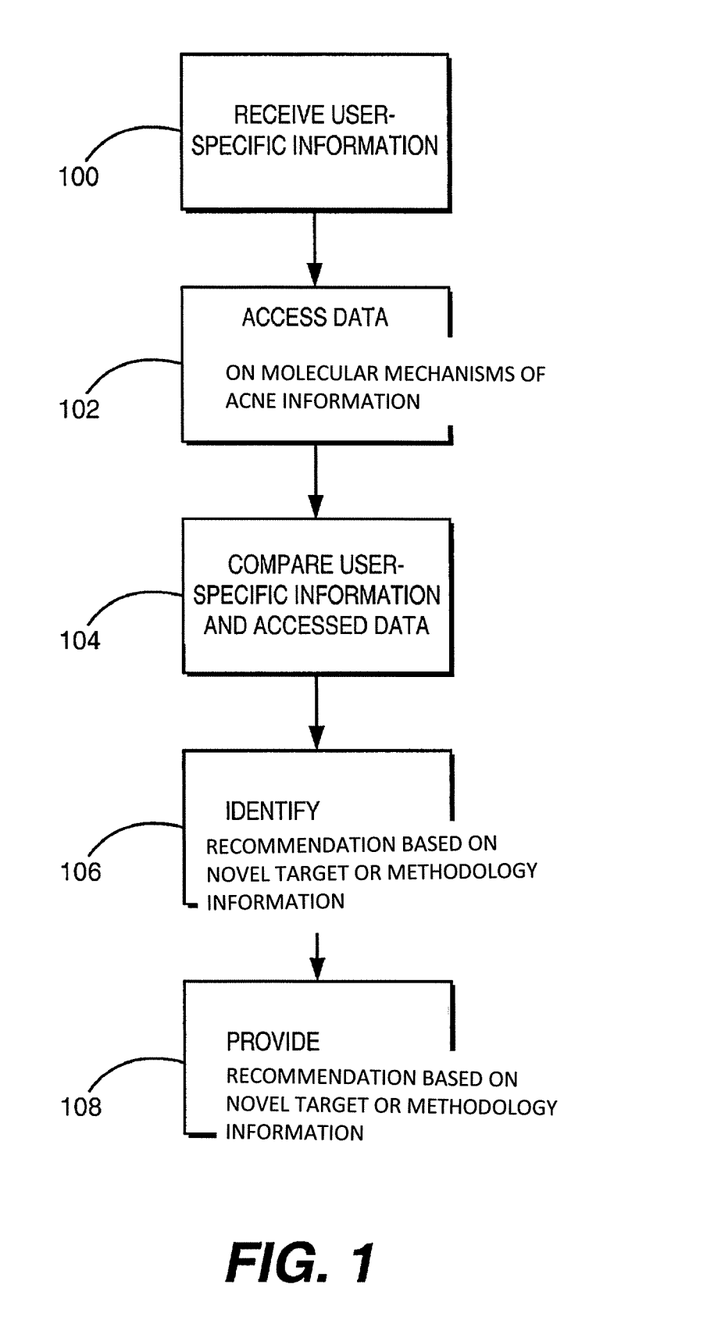
FIG. 1 is a flowchart illustrating an exemplary provision of skin care treatment recommendation consistent with one aspect of the invention.

The invention in one broad sense, may be exemplified in the flow chart of FIG. 1, where user-specific information may be received at step 100. Reception of the user-specific information may be performed using one or more of a network (described below), oral communication, visual communication, written communication, physical data carrier (described below), and/or any other means capable of conveying skin care treatment recommendation. Networks may include a local area network, a wide area network, a virtual private network, a dedicated intranet, the Internet, the Ethernet, a radio network, a telephony-based network, a cellular network, a wireless network, or any other mechanism enabling communication between two or more nodes or locations. Examples of a physical data carrier may include one or more of paper stock, an electronic data carrier, and a computer screen.

The user-specific information may be organized into categories, such as personal information. Personal information may include demographics, skin and body conditions (e.g. skin type, skin texture, skin tone, wrinkles, etc.), age, facial features, allergy information, climate information and/or lifestyle information.

Consistent with the invention, a method may also include accessing a data structure containing information reflecting relationships between categories of user-specific information and skin care treatment recommendation based on novel target or methodology identified using AI, as illustrated at step 102 in FIG. 1.

A data structure may include a read-only memory (ROM) device, random access memory (RAM) device, tape, disk drive, optical storage device, magnetic storage device, redundant array of inexpensive disks (RAID), organic storage media, computer code, constructs derived from computer code, and/or any other mechanism capable of containing information.

A method consistent with the invention may further include comparing, using an artificial intelligence engine, the received user-specific information with the accessed data, as illustrated at step 104. Comparing may include determining the appropriateness of pieces of the accessed data for the user based on the user-specific information using artificial intelligence.

Consistent with the invention, a method may additionally include identifying, using an artificial intelligence engine, skin care treatment recommendation determined by the artificial intelligence engine to be related to the user-specific information, as illustrated at step 106. The determination may involve using artificial intelligence in manners described later herein.

A method may optionally include providing identified skin care treatment recommendation to a user, as illustrated at step 108. Provision of the skin care treatment recommendation may be performed using any of the mechanisms and methods described above for reception of user-specific information.

Figure 2:
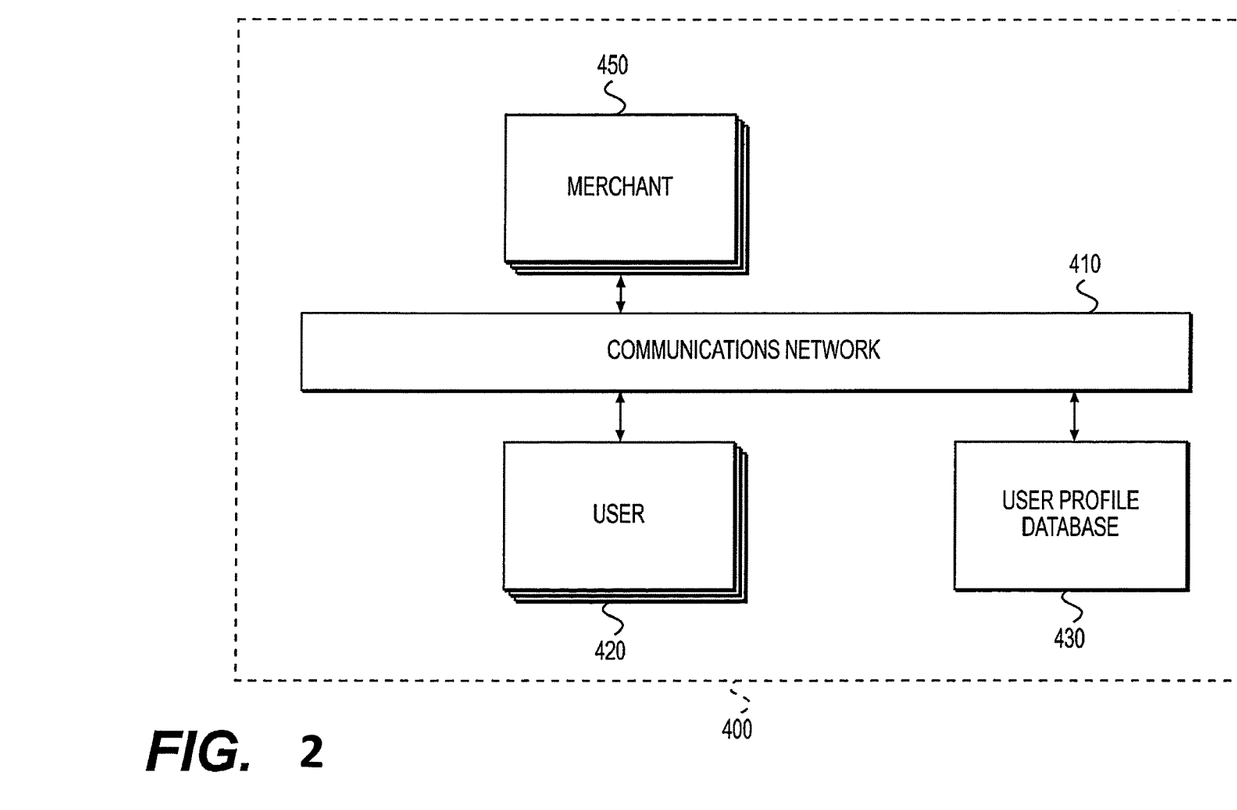
FIG. 2 is a schematic diagram of an exemplary system environment consistent with the invention.

FIG. 2 illustrates an exemplary system environment in which the invention may be implemented. For purposes of the present invention, a system 400 may be contained in a stand-alone device (e.g., a computer or a kiosk) or may be distributed over a network. For explanatory purposes, system 400 will be described in a network environment. In the network embodiment, system 400 may include a communications network 410, one or more user nodes 420, a novel target or methodology for skin care treatment database 430, and one or more merchant nodes 450. Although it is to be understood that multiple user and merchant nodes are contemplated within the scope of the invention, for explanatory purposes only a single user node 420 and merchant node 450 are illustrated in the drawings and described herein.

Communications network 410 may represent any type of network as described above. Further, any suitable combination of wired or wireless components and systems may be incorporated into communications network 410.

User node 420 may include a data processor or a computer configured with a network browser. A user may access communications network 410 to browse the site(s) of merchant node 450. For explanatory purposes, the term "user" broadly encompasses anyone accessing system 400, including an individual, a customer, a consumer, or any other entity.

Merchant node 450 may include a data processor, such as a web server, for providing information, services, and/or products. Merchant node 450 may be a computer, kiosk, a terminal, and/or other equipment capable of accessing system 400. Merchant node 450 may represent an independent retailer, a department store, a cosmetic company, a discounter, a skin care treatment salon, a skin care treatment supplier, a laboratory, and/or any other entity involved in commerce.

Figure 3:
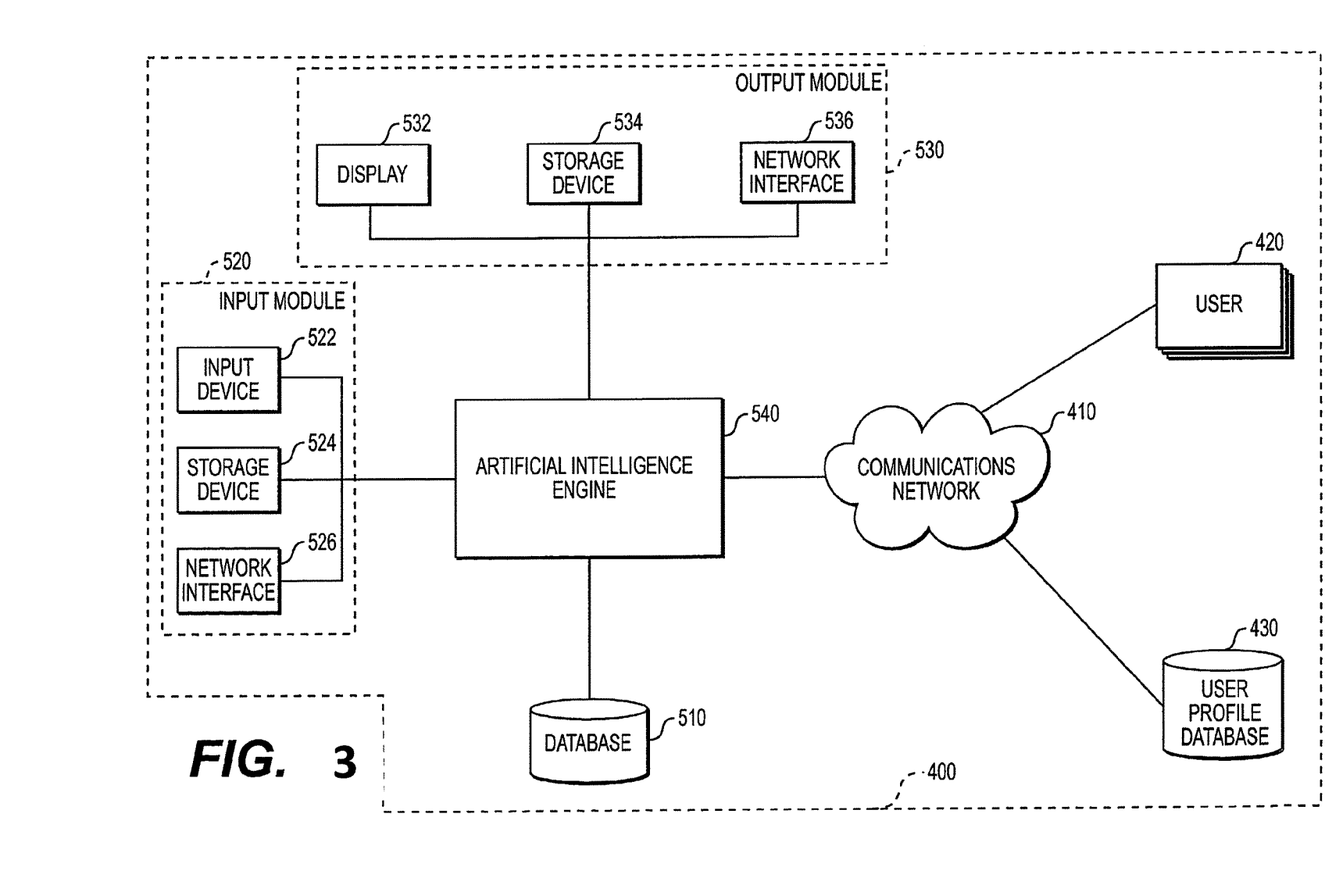
FIG. 3 is a schematic diagram of another exemplary system environment consistent with the invention.

FIG. 3 illustrates another exemplary system environment in accordance with an embodiment of the invention. As shown in FIG. 3, system 400 may include communications network 410, user node 420, novel target or methodology for skin care treatment database 430, database 510, input module 520, output module 530, and artificial intelligence engine 540.

Database 510 may contain a variety of information for analysis and computation by AI engine 540. For example, database 510 may contain information about products and services as well as expert recommendation. Database 510 may be a memory location at merchant node 450 or memory location separate from merchant node 450.

Input module 520 may be implemented with a wide variety of devices for receiving information, and may include an input device 522, a storage device 524, and a network interface 526. Input device 522 may be, for example, a keyboard, a mouse, a disk drive, a telephone, a scanner, a microphone, a web cam, and/or any other suitable input mechanism for conveying information to AI engine 540.

Likewise, storage device 524 may be implemented with a wide variety of systems, subsystems, and/or devices for providing memory or storage, including one or more of the following: read-only memory (ROM) device, random access memory (RAM) device, tape, disk drive, optical storage device, magnetic storage device, redundant array of inexpensive disks (RAID), organic storage media, and/or any other mechanism capable of providing storage or memory.

Network interface 526 may facilitate an exchange of data between communications network 410 and AI engine 540. Network interface 526 may also exchange data between input module 520 and AI engine 540. In one embodiment, communications network 410 may permit a connection to at least one or more of the networks previously described or any other mechanism for enabling communication between two or more nodes or locations and connectable to input module 520.

Output module 530 may be implemented with a wide variety of devices for providing information, and may include a display 532, a storage device 534, and a network interface 536. Display 532 may be any output device, for example, a cathode ray tube (CRT), a liquid crystal display (LCD), and/or a printing device. Storage device 534 may be similar to storage device 524. Network interface 536 may exchange data between communications network 410 and AI engine 540. Network interface 536 may also exchange data between output module 530 and AI engine 540. In some aspects, network interface 536 may be similar to network interface 526.

In one embodiment, AI engine 540 may include a data processor, a personal computer, and/or a mainframe for performing various functions and operations. AI engine 540 may be implemented, for example, by a general purpose computer or a data processor selectively activated or reconfigured by a stored computer program, or may be a specially constructed computing platform for carrying out the features and operations described herein. Moreover, AI engine 540 may be implemented or provided with a wide variety of components or systems, including one or more of the following: central processing units, co-processors, memories, registers, and/or other data processing devices and subsystems.

Figure 4:
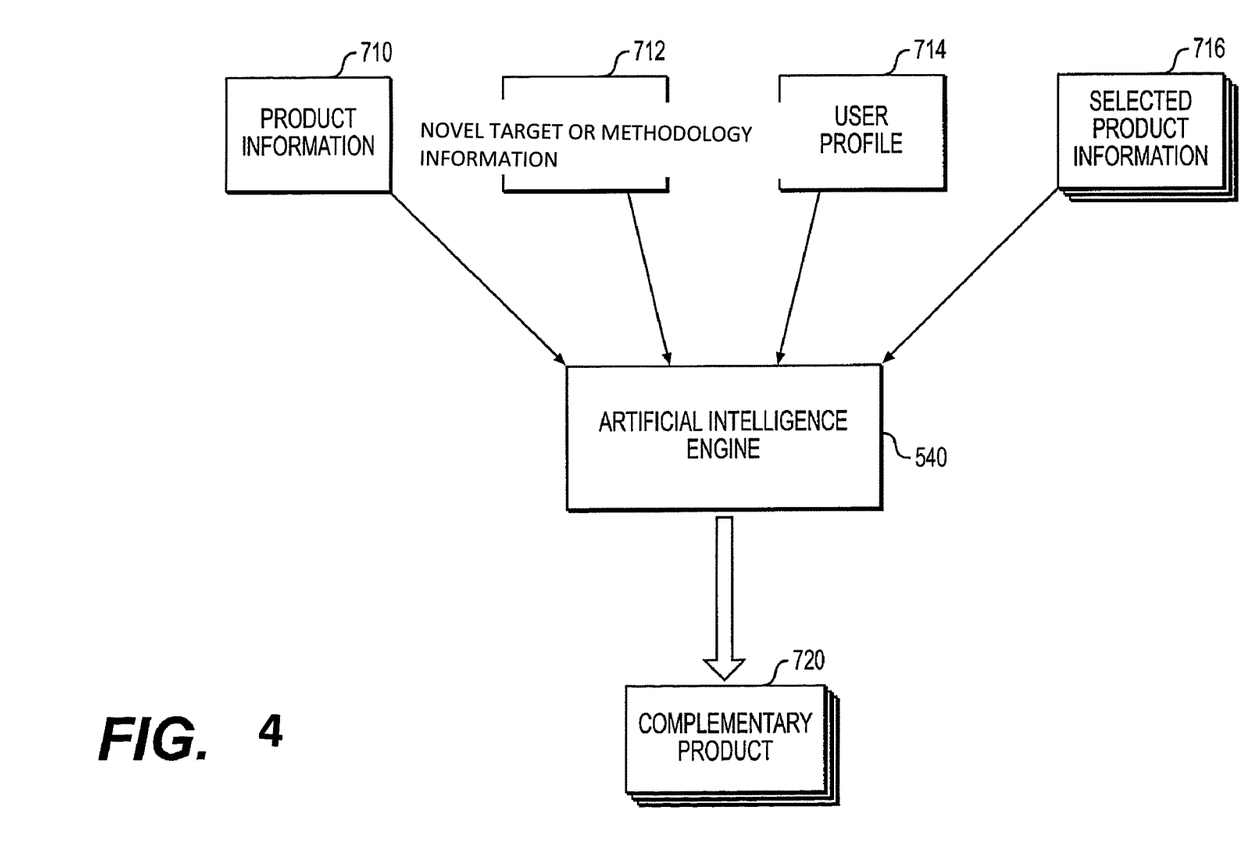
FIG. 4 is a schematic diagram of an overview of an aspect of the invention for providing recommendations of a product.

FIG. 4 illustrates, in general, one embodiment of AI engine 540. AI engine 540 may analyze, for example, one or more input information: product information 710, novel target or methodology for skin care treatment information 712, user profile 714, or selected product information 716. User profile 714 may include information related to physical characteristics, lifestyle, family history, vocation, environment, genes, mailing address, and/or any other information personal to the user. AI engine 540 may analyze any one or more of the input variables to identify one or more recommended products 720. Product information 710 and novel target or methodology for skin care treatment information 712 may be maintained at any convenient location such as database 510, merchant node 450, or a portable storage medium.

Figure 5:
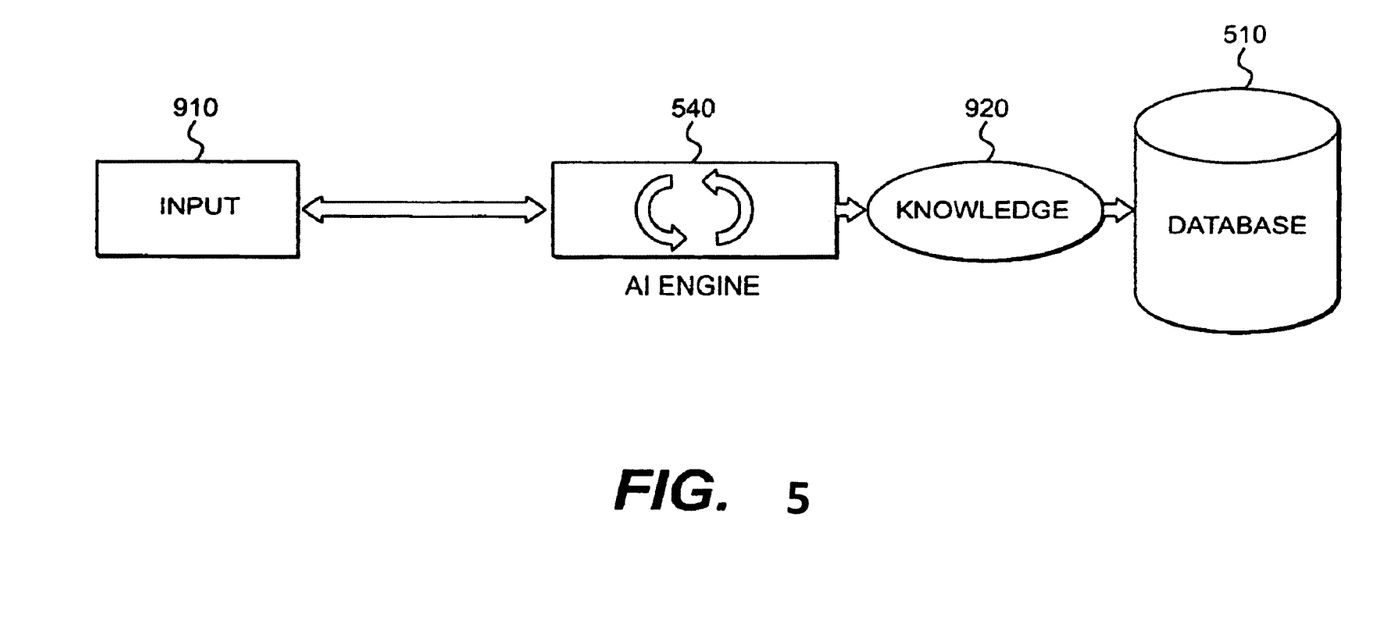
FIG. 5 is a schematic diagram of an exemplary artificial intelligence (AI) engine consistent with the invention.

FIG. 5 is an overview of an exemplary AI engine 540 based on neural networks consistent with one aspect of the invention. AI engine 540 may be trained based on input 910. Input 910 may include any information, including product information 710, novel target or methodology for skin care treatment information 712, and/or user profile 714. Using input 910, AI engine 540 may implement an iterative training process. Training may be based on a wide variety of learning rules or training algorithms.

As a result of the training, AI engine 540 may learn to modify its behavior in response to its environment, and obtain knowledge 920. Knowledge 920 may represent any information upon which AI engine 540 may determine an appropriate response to new data or situations.

As previously mentioned, for purposes of the present invention, product information 710 may be directly maintained by system 400 or indirectly maintained through a third party service. A third party service may be any entity or individual, which is not represented by any part of system 400, but provides services, products, and/or data to entities represented by any part of system 400. If a third party service maintains product information 710, such information may be provided for use by system 400 at any one time. Alternatively, the relationship may be dynamic with the third party system and may provide updates on a regular basis. The third party may provide product information 710 on a storage medium or through electronic transmission.

Figure 6:
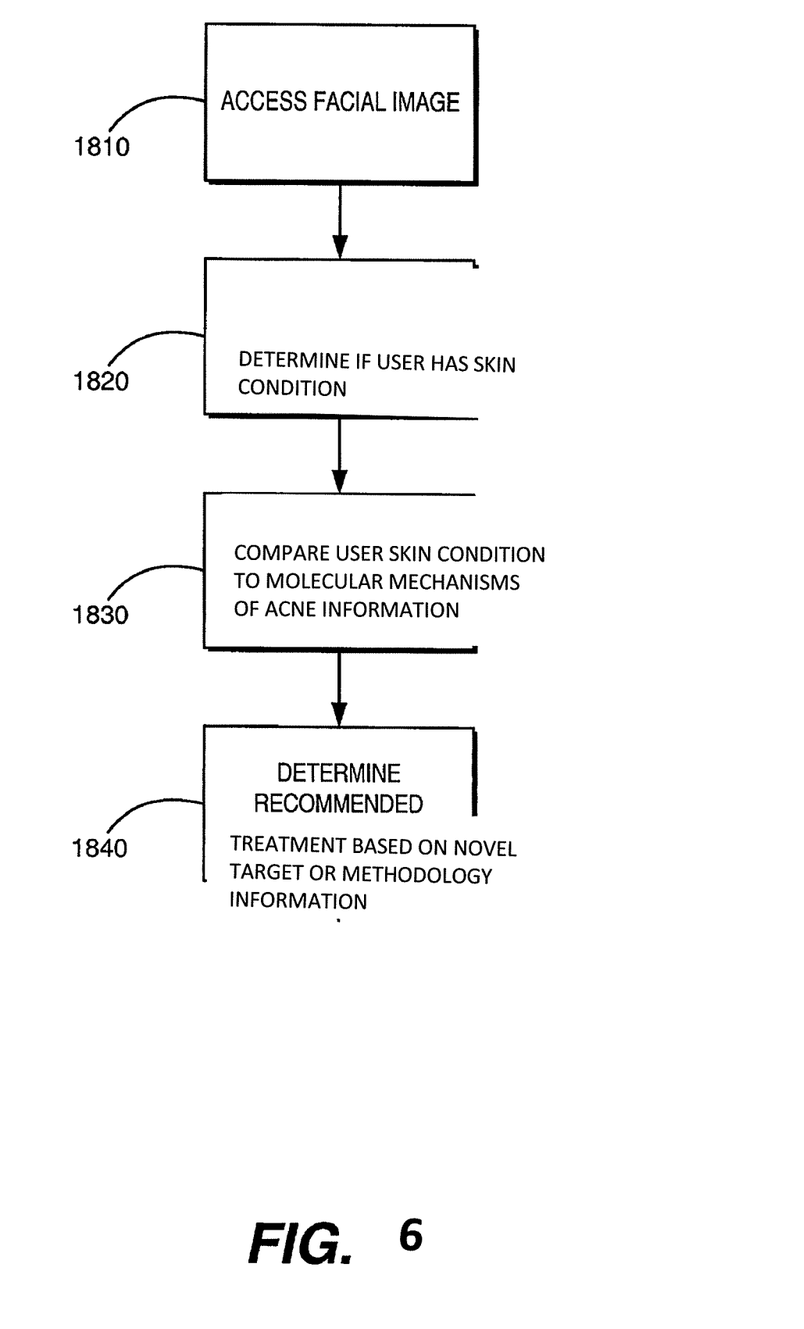
FIG. 6 is a flowchart illustrating an exemplary visual simulation according to an embodiment of the invention.

FIG. 6 is a flowchart illustrating an exemplary visual simulation according to one embodiment of the invention. As with all flowcharts contained herein, the order of the steps as presented are for exemplary purposes only and are not intended to limit the invention in its broadest sense.

As indicated in FIG. 6, regardless of system implementation details, a facial image may be accessed at step 1810. Accessing may include obtaining a facial image from a network, data structure, and/or storage medium. Examples of a network, data structure, and storage medium are previously described.

During or after receiving the facial image, the facial image may be displayed. While the term "displaying" may include a direct act of presenting content, in a broader sense, the invention is not so limited. Specifically, as used herein, forms of the word "displaying" may include indirect acts such as providing content for transmission over a network to a display unit, regardless of whether the display unit is in the custody and/or control of the sender. "Displaying" may further include preparing content for delivery to an intermediate carrier which may then transmit the content to an end user for presentation of the content on an end user's display device. Thus, any entity in a chain of delivering information for display performs an act of "displaying" within the context of this patent. This also includes parties involved in the provision of software to facilitate facial image display. Software may include computer programs, routines, and/or any instructions implementable by computer or electronic devices. As previously described, a display may include a CRT, LCD, printing device, and/or any other information output device.

A method consistent with the invention may include determining if user has a skin condition, e.g., acne vulgaris, and thus requires skin care treatment as is generally represented at step 1820 in FIG. 6.

A method consistent with the invention may also include comparing user skin condition information to molecular mechanisms of acne (step 1830). A method consistent with the invention may further include determining a recommended skin care treatment based on skin care treatment recommendation based on novel target or methodology identified using AI at step 1840. Recommendations may be provided by verbal, written, visual, or electronic communication.

It is to be further understood that the physical mechanisms (e.g. hardware, software, networks, systems) for implementing the methods of the invention are many. Networks, hardware and systems can be configured in a host of ways with software and hardware functionality residing at many alternative locations. In addition, systems other than the exemplary systems disclosed might be used to implement the invention. Therefore, it is to be understood that the methods of the invention are not limited to any particular structure.

Further, methods or portions thereof can be implemented in either an electronic environment, a physical environment, or combinations thereof.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A method of providing skin care treatment, comprising:
receiving user-specific information, wherein the user specific information includes an image of the user captured with an image capture device;
accessing a data structure containing information reflecting relationships between categories of the user-specific information and skin care treatment information, the information reflecting relationships derived from novel target or methodology for treatment of acne vulgaris obtained using artificial intelligence, wherein the novel target includes upregulated receptors on a cell and a cell originating signal;
identifying, within the accessed data structure, the novel target by predicting, by a machine-learning (ML) model, counter-expression signature effects, wherein the ML model predicts the counter-expression signature effects by concept mapping (CMAP) correlation;
classifying the identified novel target for efficacy;
comparing, using an artificial intelligence engine, the received user-specific information with the accessed data including the classified identified novel target;
identifying, using the artificial intelligence engine, skin care treatment recommendation determined by the artificial intelligence engine to be related to the user-specific information; and
providing the identified skin care treatment to the user.

2. The method of claim 1, wherein the user provides the specific information using a user interface.

3. The method of claim 1, wherein the user-specific information includes personal information of at least one of skin type, skin tone, allergy information, demographic information, climate information and lifestyle information.

4. The method of claim 1, wherein the artificial intelligence engine is based on at least one of a neural network, constraint program, fuzzy logic, classification, conventional artificial intelligence, symbolic manipulation, fuzzy set theory, evolutionary computation, cybernetics, data mining, approximate reasoning, derivative-free optimization, and soft computing.

5. The method of claim 1 conducted, at least in part, in a network environment, wherein receiving user-specific information occurs via a network and in at least one location remote from the user, and wherein providing occurs via the network.

6. The method of claim 1, wherein the skin care treatment includes a product recommendation.

7. The method of claim 1, wherein the method is employed to treat at least one condition selected from the group consisting of pore size, elasticity, dryness, cellulitis, sweating, aging, wrinkles, melanoma, exfoliation, desquamation, homogeneity of color, micro-circulation, shininess, softness, smoothness, matitty, hydration, sebum production, cleanliness, irritation, redness, vasomotion, vasodilation, vasoconstriction, pigmentation, freckles and acne vulgaris.

8. The method of claim 7, further comprising presenting to the subject information about at least one product for treating the at least one condition.

9. A method for educating a consumer about skin care treatment comprising:
receiving a request from a consumer for information regarding skin care treatment;
receiving from the consumer a description of one or more physical characteristics associated with the consumer and related to the skin care treatment and user specific information, wherein the user specific information includes an image of the user captured with an image capture device;
determining, by a processor a novel target or methodology for treatment of acne vulgaris obtained by predicting, by a machine-learning (ML) model, counter-expression signature effects, wherein the ML model predicts the counter-expression signature effects by concept mapping (CMAP) correlation, wherein the novel target includes upregulated receptors on a cell and a cell originating signal;
classifying the identified novel target for efficacy; and
informing the consumer of the classified identified novel target or methodology for treatment of acne vulgaris.

\* \* \* \* \*